United States Patent
Bayer et al.

(12) 
(10) Patent No.: US 6,274,586 B1
(45) Date of Patent: Aug. 14, 2001

(54) COMBATTING PARASITIC FUNGI WITH A COMBINATION OF AN ACTIVE AGENT INHIBITING RESPIRATION IN THE CYTOCHROME COMPLEX III AND OF FENAZAQUINE

(75) Inventors: Herbert Bayer; Hubert Sauter, both of Mannheim; Eberhard Ammermann, Heppenheim; Gisela Lorenz, Hambach; Siegfried Strathmann, Limburgerhof; Harald Köhle, Bobenheim; Günter Retzlaf, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/571,402

(22) Filed: May 15, 2000

Related U.S. Application Data

(62) Division of application No. 09/029,951, filed as application No. PCT/EP96/04013 on Sep. 12, 1996.

(30) Foreign Application Priority Data

Sep. 25, 1995 (DE) .............................................. 195 35 516

(51) Int. Cl.$^7$ .................................................. A01N 43/54
(52) U.S. Cl. ........................................... 514/259; 514/259
(58) Field of Search ............................................... 514/259

(56) References Cited

U.S. PATENT DOCUMENTS

| | | | |
|---|---|---|---|
| 5,508,285 | 4/1996 | Eicken et al. | 514/275 |
| 5,589,479 | 12/1996 | Eicken et al. | 514/275 |
| 5,591,747 | 1/1997 | Eicken et al. | 514/275 |
| 6,083,946 | 7/2000 | Müller et al. | |

FOREIGN PATENT DOCUMENTS

| | | | |
|---|---|---|---|
| 0326329 | * | 2/1989 | (EP) . |
| 0 326 329 | | 8/1989 | (EP) . |
| 0382375 | * | 8/1990 | (EP) . |
| 0 382 375 | | 8/1990 | (EP) . |
| 0 398 692 | | 11/1990 | (EP) . |
| 0 642 735 | | 3/1995 | (EP) . |

OTHER PUBLICATIONS

Brandl et al., Dechema Monographie 129, 27–38 (1993).

Clough, Natural Product Reports, 10(1), 565–574 (1993).

Svoboda, Biochem. Soc. Trans.22, 635–641 (1994).

Jewess, Biochem. Soc. Trans.22, 247–251 (1994).

The Pesticide Manual, 10th Ed. 426–427 (1994).

*Mitt. Biol. Bundesanstalt, Landforstwirsch., 301, p 397, p. 411 (1994).

* cited by examiner

*Primary Examiner*—Sabiha Qazi
(74) *Attorney, Agent, or Firm*—Keil & Weinkauf

(57) ABSTRACT

The present nvention relates to compositions for controlling harmful fungi which comprise, as active ingredients, at least one compound which inhibits respiration on the cytochrome complex III and fenazaquin. The compositions according to the invention are useful in particular for controlling botrytis.

20 Claims, No Drawings

COMBATTING PARASITIC FUNGI WITH A COMBINATION OF AN ACTIVE AGENT INHIBITING RESPIRATION IN THE CYTOCHROME COMPLEX III AND OF FENAZAQUINE

This is a Divisional Application of application Ser. No. 09/029,951, filed on Mar. 17, 1998, which is a national stage application under 35 U.S.C. §371 of PCT 96/04,013, filed on Sep. 12, 1996.

The present invention relates to compositions for controlling harmful fungi and to methods of controlling harmful fungi using such compositions.

The literature discloses that active ingredients which inhibit the cytochrome $bc_1$ conplex (cytochrome complex III) can be employed as fungicides [cf. U. Brandt, U. Haase, H. Schägger, G. von Jagow: "Spezifität und Wirkmechanismus der Strobilurine" (specificity and Mechanism of Action of the Strobilurins), Dechema Monograph Vol. 129, 27–38, V C H Verlagsgesellschaft Weinheim, 1993; J. M. Clough: Natural Product Reports, 1993, 565–574; F. Röhl, H. Sauter: Biochem. Soc. Trans. 22, 635 (1993)].

However, when using these active ingredients as fungicides, it has emerged that their activity is only transient, i.e. that renewed growth of the fungi was observed after a short time.

It is therefore an object of the present invention to provide an improved possibility of controlling harmful fungi, in particular botrytis.

Surprisingly, we have found that this object is achieved by a composition which comprises an active ingredient which inhibits respiration on the cytochrome complex III in combination with fenazaquin, which is known as being acaricidally active (cf. The Pesticide Manual, 10th Edition, 1994; CAS reg. No. 120928-09-8).

The present invention therefore relates to compositions for controlling harmful fungi which comprise, in a solid or liquid carrier, a) at least one active ingredient I, which inhibits respiration on the cytochrome complex III, and b) fenazaquin, of the formula

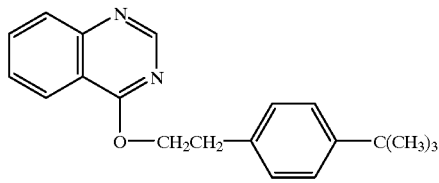

The active ingredient I is preferably a compound of the formula. IA or IB:

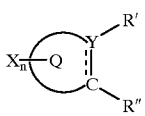

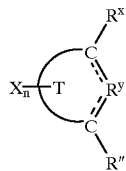

where ... is a double or single bond;

R' is —C[CO$_2$CH$_3$]=CHOCH$_3$, —C[CO$_2$CH$_3$]=NOCH$_3$, —C[CONHCH$_3$]=NOCH$_3$, —C[CO$_2$CH$_3$]=CHCH$_3$, —C[CO$_2$CH$_3$]=CHCH$_2$CH$_3$, —C[COCH$_3$]=NOCH$_3$, —C[COCH$_2$CH$_3$]=NOCH$_3$, —N(OCH$_3$)—CO$_2$CH$_3$, —N(CH$_3$)—CO$_2$CH$_3$ or —N(CH$_2$CH$_3$)—CO$_2$CH$_3$;

R" is an organic radical which is bonded directly or via an oxy, mercapto, amino, or alkylamino group, or together with a group X and the ring Q or T to which they are bonded can contain an unsubstituted or substituted bicyclic, partially or fully unsaturated system which, besides carbon ring members, can have 1, 2 or 3 hetero atoms independently selected from amongst oxygen, sulfur and nitrogen;

R$^x$ is —OC[CO$_2$CH$_3$]=CHOCH$_3$, —OC[CO$_2$CH$_3$]=CHCH$_3$, —OC[CO$_2$CH$_3$]=CHCH$_2$CH$_3$, —SC[CO$_2$CH$_3$]=CHOCH$_3$, —SC[CO$_2$CH$_3$]=CHCH$_3$, —SC[CO$_2$CH$_3$]=CHCH$_2$CH$_3$, —N(CH$_3$)C[CO$_2$CH$_3$]=CHOCH$_3$, —N(CH$_3$)C[CO$_2$CH$_3$]=NOCH$_3$, —CH$_2$C[CO$_2$CH$_3$]=CHOCH$_3$, —CH$_2$C[CO$_2$CH$_3$]=NOCH$_3$ or —CH$_2$C[CONHCH$_3$]=NOCH$_3$;

R$^y$ is oxygen, sulfur, =CH— or =N—;

n is 0, 1, 2 or 3, it being possible for the radicals X to be identical or different if n>1;

X is cyano, nitro, halogen, alkyl, haloalkyl, alkoxy, haloalkoxy, alkylthio, or, if n>1, a $C_3$–$C_5$-alkylene, $C_3$–$C_5$-alkenylene, oxy-$C_2$–$C_4$-alkylene, oxy-$C_1$–$C_3$-alkyleneoxy, oxy-$C_2$–$C_4$-alkenylene, oxy-$C_2$–$C_4$-alkenyleneoxy or butadienediyl group which is bonded to two adjacent C atoms of the phenyl ring, it being possible for these chains, in turn, to have attached to them one to three radicals which, independently of one another, are selected from amongst halogen, alkyl, haloalkyl, alkoxy, haloalkoxy and alkylthio;

Y is=C— or —N—;

Q is phenyl, pyrrolyl, thienyl, furyl, pyrazolyl, imidazolyl, oxazolyl, isoxazolyl, thiazolyl, thiadiazolyl, triazolyl, pyridinyl, 2-pyridinyl, pyrimidinyl or triazinyl; and T is phenyl, oxazolyl, thiazolyl, thiadiazolyl, oxadiazolyl, pyridinyl, pyrimidinyl or triazinyl.

The substituent R" is, in particular, an alkyl, alkenyl, alkynyl, aryl, hetaryl, arylalkyl, hetarylalkyl, arylalkenyl, hetarylalkenyl, arylalkynyl or hetarylalkynyl radical which may be interrupted by one or more groups selected from amongst O, S, SO, SO$_2$, NR (R=H or alkyl), CO, COO, OCO, CONH, NHCO and NHCONH, or a radical of the formulae which are as defined below CH$_2$ON=CR$^\alpha$CR$^\beta$ or $CH_2$ON=CR$^\delta$CR$^\delta$=NOR$^\epsilon$. These radicals may also have one or more (preferably 1, 2 or 3) substituents which, independently of one another, are selected from amongst alkyl, alkoxy, halogen, haloalkyl (in particular CF$_3$ and CHF$_2$) and aryl. The latter, in turn, can have, 1, 2 or 3 substituents which, independently of one another, are selected from amongst halogen, haloalkyl (in particular $CF_3$ and $CHF_2$), phenyl, CN and phenoxy.

Such compounds and their preparation are described in the literature given in Tables I.1 to I.8 below. Compounds which are not described in these tables can be prepared by similar methods.

Halogen within the scope of the present invention is fluorine, chlorine, bromine and iodine, in particular fluorine, chlorine and bromine.

The term "alkyl" encompasses straight-chain and branched alkyl groups. They are preferably straight-chain or branched $C_1$–$C_{12}$-alkyl and in particular $C_1$–$C_6$-alkyl groups. Examples of alkyl groups are alkyl such as, in particular, methyl, ethyl, propyl, 1-methylethyl, butyl, 1-methylpropyl, 2-methylpropyl 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated by one or more halogen atoms, in particular fluorine and chlorine. There are preferably 1 to 3 halogen atoms present, the difluoromethyl or trifluoromethyl group being specially preferred.

What has been said above for the alkyl group and haloalkyl group applies analogously to the alkyl and haloalkyl group in alkoxy, haloalkoxy, alkylthio and haloalkylthio or similar groups.

The alkenyl group encompasses straight-chain and branched alkenyl groups. They are preferably straight-chain or branched $C_3$–$C_{12}$-alkenyl groups, in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1, 1-dimethyl-3-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group can be partially or fully halogenated by one or more halogen atoms, in particular fluorine and chlorine. It has preferably 1 to 3 halogen atoms.

The alkynyl group encompasses straight-chain and branched alkynyl groups. They are preferably straight-chain or branched $C_3$–$C_{12}$-alkynyl groups, in particular $C_3$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

What has been said above about the alkenyl group and its halogen substituents, and about the alkynyl group, applies analogously to alkenyloxy and alkynyloxy.

The cycloalkyl group is preferably a $C_3$–$C_6$-cycloalkyl group, such as cyclopropyl, cyclobutyl, cyclopentyl or cyclohexyl. If the cycloalkyl group is substituted, it has preferably 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it has preferably 1 to 3 $C_1$–$C_4$-alkyl radicals as substituents.

A cycloalkoxy group is preferably a $C_5$–$C_6$-cycloalkoxy group, such as cyclopentyloxy or cyclohexyloxy. If the cycloalkoxy group is substituted, it has preferably 1 to 3 $C_1$–$C_4$-alkyl radicals as substituents.

The cycloalkenyloxy group is preferably a $C_5$–$C_6$-cycloalkenyloxy group, such as cyclopentyloxy or cyclohexyloxy. If the cycloalkenyloxy group is substituted, it has preferably 1 to 3 $C_1$–$C_4$-alkyl radicals as substituents. Aryl is preferably phenyl.

Hetaryl is preferably a 5- or 6-membered aromatic heterocycle which has 1, 2 or 3 hetero atoms which, independently of one another, are selected from amongst N, O and S. It is, in particular, pyridynyl, pyrimidynyl, thiazolyl or pyrazolyl.

Heterocyclyl is preferably a 5- or 6-membered saturated or unsaturated heterocycle which has 1, 2 or 3 hetero atoms which, independently of one another, are selected from amongst N, O and S. It is, in particular, one of the dihydro, tetrahydro and hexahydro derivatives of the radical mentioned under "hetaryl". Preferred are pyrrolidynyl, tetrahydrofuranyl, imidazolidynyl, pyrazolidynyl, oxazolidynyl, isoxazolidynyl, thiazolidynyl, isothiazolidynyl, piperidynyl or morpholynyl.

In a preferred embodiment, the compositions according to the invention comprise a compound of the formula IA or IB where R" is aryloxy, hetaryloxy, aryloxymethylene, hetaryloxymethylene, arylethenylene or hetarylethenylene, it being possible for these radicals to have 1, 2 or 3 substituents which, independently of one another, are selected from amongst alkxl, halogen, $CF_3$, $CHF_2$, CN, alkoxy and phenyl which, in turn, can have 1, 2 or 3 substituents which, independently of one another, are selected from amongst halogen, $CF_3$, $CHF_2$, phenyl, CN, phenoxy, alkyl, alkoxy and haloalkoxy;
or R" is

$$CH_2ON=CR^\alpha R^\beta \text{ or } CH_2ON=CR^\gamma CR^\epsilon NOR^\epsilon$$

where $R^\alpha$ is alkyl;
$R^\beta$ is phenyl, pyridyl or pyrimidyl which may have 1, 2 or 3 substituents which, independently of one another, are selected from amonst alkyl, alkoxy, halogen, haloalkoxy, $CF_3$ and $CHF_2$;
$R^\gamma$ is alkyl, alkoxy, halogen, haloalkyl or hydrogen;
$R^\delta$ is hydrogen, cyano, halogen, alkyl, alkoxy, alkylthio, alkylamino, dialkylamino, alkenyl, alkenyloxy, alkenylthio, alkenylamino, N-alkenyl-N-alkylamino, alkynyl, alkynyloxy, alkynylthio, alkynylamino, N-alkynyl-N-alkylamino, it being possible for the hydrocarbon radicals of these groups to be partially or fully halogenated and/or to have attached to them 1, 2 or 3 radicals which, independently of one another, are selected from amongst cyano, nitro, hydroxyl, alkoxy, haloalkoxy, alkoxycarbonyl, alkylthio, alkylamino, di-alkylamino, alkenyloxy, cycloalkyl, cycloalkyloxy, heterocyclyl, heterocyclyloxy, aryl, aryloxy, arylalkoxy, hetaryl, hetaryloxy and hetarylalkoxy, it being possible for the cyclic radicals, in turn, to be partially or fully halogenated and/or to have attached to them 1, 2 or 3 groups which, independently of one another, are selected from amongst cyano, nitro, hydroxyl, alkyl, haloalkyl, cycloalkyl, alkoxy, haloalkoxy, alkoxycarbonyl, alkylthio, alkylamino, dialkylamino, alkenyl and alkenyloxy;

or is cycloalkyl, cycloalkyloxy, cycloalkylthio, cycloalkylamino, N-cycloalkyl-N-alkylamino, heterocyclyl, heterocyclyloxy, heterocyclylthio, heterocyclylamino, N-heterocyclyl-N-alkylamino, aryl, aryloxy, arylthio, arylamino, N-aryl-N-alkylamino, hetaryl, hetaryloxy, hetarylthio, hetarylamino or N-hetaryl-N-alkylamino, it being possible for the cyclic radicals to be partially or fully halogenated and/or to have attached to them 1, 2 or 3 groups which, independently of one another, are selected from amongst cyano, nitro, hydroxyl, alkyl, haloalkyl, cycloalkyl, alkoxy, haloalkoxy, alkoxycarbonyl, alkylthio, alkylamino, di-alkylamino, alkenyl, alkenyloxy, benzyl, benzyloxy, aryl, aryloxy, hetaryl and hetaryloxy, it being possible for the aromatic radicals, in turn, to be partially or fully halogenated and/or to have attached to them 1, 2 or 3 of the following groups: cyano, alkyl, haloalkyl, alkoxy, nitro;

$R^\epsilon$ is alkyl, alkenyl or alkynyl, it being possible for these groups to be partially or fully halogenated and/or to have attached to them 1, 2 or 3 of the following radicals: cyano, alkoxy, cycloalkyl.

Especially preferred compounds of the formula IA or IB are those where

R" has one of the following meanings:
a) phenyloxymethylene, pyridinyloxymethylene, pyrimidynyloxymethylene or pyrazolyloxymethylene, it being possible for the aromatic radical to have 1, 2 or 3 substituents which, independently of one another, are selected from amongst alkyl, halogen, $CF_3$, $CHF_2$, —C($CH_3$)—$NOCH_3$ and phenyl which is unsubstituted or substituted by 1, 2 or 3 halogen atoms and/or alkyl groups;
b) phenoxy or pyrimidynyloxy, unsubstituted or substituted by 1, 2 or 3 halogen atoms or one phenoxy radical which may have a halogen or cyano substituent;
c) phenylethenylene or pyrazolylethenylene, it being possible for the phenyl or pyrazolyl radical to have 1, 2 or 3 substituents which, independently of one another, are selected from amongst halogen, $CF_3$, $CHF_2$ and phenyl.
d) $CH_2ON=CR^\alpha R^\beta$,
where $R^\alpha$ is alkyl; and
$R^\beta$ is phenyl which may have 1, 2 or 3 substituents which, independently of one another, are selected from amongst alkyl, halogen, $CF_3$ and $CHF_2$, or is pyrimidynyl which is unsubstituted or substituted by 1 or 2 alkoxy radicals;
e) $CH_2ON=CR^\gamma CR^\delta=NOR^\epsilon$, where $R^\gamma$ is alkyl, alkoxy or halogen; $R^\delta$ is alkyl, cyano, halogen, alkoxy, alkenyl or phenyl which is unsubstituted or substituted by 1, 2 or 3 halogen atoms; and $R^\epsilon$ is alkyl.

Particularly preferred compounds are those of the formula IA, where Q is phenyl and n is 0. Especially suitable active ingredients I are compiled in the tables which follow.

TABLE I.1A

Compounds of the formula IA, where Q is phenyl, R' is —C($CO_2CH_3$)=$CHOCH_3$, n has the value 0, R" is unsubstituted or substituted (het)aryloxymethylene, the unsubstituted or substituted (het)aryl group having the meanings given below

| No. | Unsubst. or subst. (het)aryl | Reference |
| --- | --- | --- |
| I.1A-1 | 2-$CH_3$—$C_6H_4$ | EP-A 226 917 |
| I.1A-2 | 2,5-($CH_3$)$_2$—$C_6H_3$ | EP-A 226 917 |
| I.1A-3 | 2-$CH_3$,4-C[$CH_3$]=$NOCH_3$—$C_6H_3$ | EP-A 386 561 |
| I.1A-4 | 2-$CH_2CH_2CH_3$,6-$CF_3$-pyrimidin-4-yl | EP-A 407 873 |
| I.1A-5 | 2,4-($CH_3$)$_2$—$C_6H_3$ | EP-A 226 917 |

TABLE I.1B

Compounds of the formula IA, R' is —C($CO_2CH_3$)=$CHOCH_3$, where Q is phenyl, n has the value 0, R" is unsubstituted or substituted (het)aryloxy the unsubstituted or substituted (het)aryl group having the meanings given below

| No. | Unsubst. or subst. (het)aryl | Reference |
| --- | --- | --- |
| I.1B-1 | $C_6H_5$ | EP-A 178 826 |
| I.1B-2 | 6-[2-CN—$C_6H_4$—O]-pyrimidin-4-yl | EP-A 382 375 |

TABLE I.1C

Compounds of the formula IA, R' is —C($CO_2CH_3$)=$CHOCH_3$, where Q is phenyl, n has the value 0, R" is unsubstituted or substituted (het)arylethenylene the unsubstituted or substituted (het)aryl group having the meanings given below

| No. | Unsubst. or subst. (het)aryl | Reference |
| --- | --- | --- |
| I.1C-1 | 1-(2,4-$Cl_2$—$C_6H_3$),5-$CF_3$-pyrazol-4-yl | EP-A 528 245 |
| I.1C-2 | 1-(4-Cl—$C_6H_4$)-pyrazol-4-yl | EP-A 378 755 |
| I.1C-3 | 3-$CF_3$—$C_6H_4$ | EP-A 203 606 |
| I.1C-4 | 3-Cl—$C_6H_4$ | EP-A 203 606 |
| I.1C-5 | 4-$C_6H_5$—$C_6H_4$ | EP-A 203 606 |

TABLE I.1D

Compounds of the formula IA, where Q is phenyl, R' is —C($CO_2CH_3$)=$CHOCH_3$, n has the value 0, R" is $CH_2ON=CR^\alpha R^\beta$, $R^\alpha$ and $R^\beta$ having the meanings given below

| No. | $R^\alpha$ | $R^\beta$ | Reference |
| --- | --- | --- | --- |
| I.1D-1 | $CH_3$ | 4-Cl—$C_6H_4$ | EP-A 370 629 |
| I.1D-2 | $CH_3$ | 3-$CF_3$—$C_6H_4$ | EP-A 370 629 |
| I.1D-3 | $CH_3$ | 4-$OCH_2CH_3$-pyrimidin-2-yl | WO-A 92/18,487 |

TABLE I.1E

Compounds of the formula IA, where Q is phenyl, R' is
—C(CO$_2$CH$_3$)=CHOCH$_3$, n has the value 0, R" is
CH$_2$ON=CR$^\gamma$CR$^\delta$=NOR$^\epsilon$, R$_\gamma$, R$^\delta$ and R$^\epsilon$
having the meanings given below

| No. | R$^\gamma$ | R$^\delta$ | R$^\epsilon$ | Reference |
|---|---|---|---|---|
| I.1E-1 | CH$_3$ | CH$_3$ | CH$_3$ | WO-A 95/21153 |
| I.1E-2 | CH$_3$ | CH$_3$ | CH$_2$CH$_3$ | WO-A 95/21153 |
| I.1E-3 | CH$_3$ | C$_6$H$_5$ | CH$_3$ | WO-A 95/21153 |
| I.1E-4 | CH$_3$ | C$_6$H$_5$ | CH$_2$CH$_3$ | WO-A 95/21153 |
| I.1E-5 | CH$_3$ | 4-Cl—C$_6$H$_4$ | CH$_3$ | WO-A 95/21153 |
| I.1E-6 | CH$_3$ | 4-Cl—C$_6$H$_4$ | CH$_2$CH$_3$ | WO-A 95/21153 |

TABLE I.2A

Compounds of the formula IA, where Q is phenyl, R' is
—C(CO$_2$CH$_3$)=NOCH$_3$, n has the value 0, R" is unsubstituted
or substituted (het)aryloxymethylene, the unsubstituted or substituted
(het)aryl group having the meanings given below

| No. | Unsubst. or subst. (het)aryl | Reference |
|---|---|---|
| I.2A-1 | 2-CH$_3$—C$_6$H$_4$ | EP-A 253 213 |
| I.2A-2 | 2,5-(CH$_3$)$_2$—C$_6$H$_3$ | EP-A 400 417 |
| I.2A-3 | 2,4-(CH$_3$)$_2$—C$_6$H$_3$ | EP-A 400 417 |
| I.2A-4 | 2,3,5-(CH$_3$)$_3$—C$_6$H$_2$ | EP-A 400 417 |
| I.2A-5 | 2-Cl,5-CH$_3$—C$_6$H$_3$ | EP-A 400 417 |
| I.1A-6 | 2-CH$_3$,4-C[CH$_3$]=NOCH$_3$—C$_6$H$_3$ | EP-A 386 561 |

TABLE I.2B

Compounds of the formula IA, where Q is phenyl, R' is
—C(CO$_2$CH$_3$)=NOCH$_3$, n has the value 0, R" is unsubstituted or
substituted (het)aryloxy, the unsubstituted or substituted (het)aryl group
having the meanings given below

| No. | Unsubst. or subst. (het)aryl | Reference |
|---|---|---|
| I.2B-1 | C$_6$H$_5$ | EP-A 253 213 |
| I.2B-2 | 6-[2-CN—C$_6$H$_4$—O]-pyrimidin-4-yl | EP-A 468 684 |

TABLE I.2C

Compounds of the formula IA, where Q is phenyl, R' is
—C(CO$_2$CH$_3$)=NOCH$_3$, n has the value 0, R" is
CH$_2$ON=CR$^\alpha$R$^\beta$, R$^\alpha$ and R$^\beta$ having the meanings given below

| No. | R$^\alpha$ | R$^\beta$ | Reference |
|---|---|---|---|
| I.2C-1 | CH$_3$ | 4-Cl—C$_6$H$_4$ | EP-A 463 488 |
| I.2C-2 | CH$_3$ | 3-Cl—C$_6$H$_4$ | EP-A 463 488 |
| I.2C-3 | CH$_3$ | 4-CF$_3$—C$_6$H$_4$ | EP-A 463 488 |
| I.2C-4 | CH$_3$ | 3-CF$_3$—C$_6$H$_4$ | EP-A 463 488 |
| I.2C-5 | CH$_3$ | 4-CH$_3$—C$_6$H$_4$ | EP-A 463 488 |
| I.2C-6 | CH$_3$ | 4-OCH$_2$CH$_3$-pyrimidin-2-yl | EP-A 472 300 |
| I.2C-7 | CH$_3$ | 3,5-Cl$_2$—C$_6$H$_3$ | EP-A 463 488 |

TABLE I.2D

Compounds of the formula IA, where Q is phenyl, R' is
—C(CO$_2$CH$_3$)=NOCH$_3$, n has the value 0, R" is
CH$_2$ON=CR$^\gamma$CR$^\delta$=NOR$^\epsilon$, R$_\gamma$, R$^\delta$ and R$^\epsilon$
having the meanings given below

| No. | R$^\gamma$ | R$^\delta$ | R$^\epsilon$ | Reference |
|---|---|---|---|---|
| I.2D-1 | CH$_3$ | CH$_3$ | CH$_3$ | WO-A 95/21153 |
| I.2D-2 | CH$_3$ | CH$_3$ | CH$_2$CH$_3$ | WO-A 95/21153 |
| I.2D-3 | CH$_3$ | C$_6$H$_5$ | CH$_3$ | WO-A 95/21153 |
| I.2D-4 | CH$_3$ | C$_6$H$_5$ | CH$_2$CH$_3$ | WO-A 95/21153 |
| I.2D-5 | CH$_3$ | 4-Cl—C$_6$H$_4$ | CH$_3$ | WO-A 95/21153 |
| I.2D-6 | CH$_3$ | 4-Cl—C$_6$H$_4$ | CH$_2$CH$_3$ | WO-A 95/21153 |

TABLE I.3A

Compounds of the formula IA, where Q is phenyl, R' is
—C(CONHCH$_3$)=NOCH$_3$, n has the value 0, R" is unsubstituted
or substituted (het)aryloxymethylene, the unsubstituted or substituted
(het)aryl group having the meanings given below

| No. | Unsubst. or subst. (het)aryl | Reference |
|---|---|---|
| I.3A-1 | 2-CH$_3$—C$_6$H$_4$ | EP-A 477 631 |
| I.3A-2 | 2,5-(CH$_3$)$_2$—C$_6$H$_3$ | EP-A 477 631 |
| I.3A-3 | 2,4-(CH$_3$)$_2$—C$_6$H$_3$ | EP-A 477 631 |
| I.3A-4 | 2,3,5-(CH$_3$)$_3$—C$_6$H$_2$ | EP-A 477 631 |
| I.3A-5 | 2-CH$_3$,4-C[CH$_3$]=NOCH$_3$—C$_6$H$_3$ | EP-A 579 124 |
| I.3A-6 | 1-[4-Cl—C$_6$H$_4$]-pyrazol-3-yl | WO-A 94/19331 |
| I.3A-7 | 1-[2,4-Cl$_2$—C$_6$H$_3$]-pyrazol-3-yl | WO-A 94/19331 |

TABLE I.3B

Compounds of the formula IA, where Q is phenyl, R' is
—C(CONHCH$_3$)=NOCH$_3$, n has the value 0, R" is unsubstituted
or substituted (het)aryloxy, the unsubstituted or substituted
(het)aryl group having the meanings given below

| No. | Unsubst. or subst. (het)aryl | Reference |
|---|---|---|
| I.3B-1 | C$_6$H$_5$ | EP-A 398 692 |
| I.3B-2 | 6-[2-CN—C$_6$H$_4$—O]-pyrimidin-4-yl | GB-A 2 253 624 |

TABLE I.3C

Compounds of the formula IA, where Q is phenyl, R' is
—C(CONHCH$_3$)=NOCH$_3$, n has the value 0, R" is unsubstituted
or substituted (het)arylethenylene, the unsubstituted or substituted
(het)aryl group having the meanings given below

| No. | Unsubst. or subst. (het)aryl | Reference |
|---|---|---|
| I.3C-1 | 1-[2,4-Cl$_2$—C$_6$H$_3$],5-CF$_3$-pyrazol-4-yl | DE-A 44 23 615.8 |

TABLE I.3D

Compounds of the formula IA, where Q is phenyl, R' is
—C(CONHCH$_3$)=NOCH$_3$, n has the value 0, R" is
CH$_2$ON=CR$^\alpha$R$^\beta$, R$^\alpha$ and R$^\beta$ having the meanings given below

| No. | R$^\alpha$ | R$^\beta$ | Reference |
|---|---|---|---|
| I.3D-1 | CH$_3$ | 4-Cl—C$_6$H$_4$ | EP-A 463 488 |
| I.3D-2 | CH$_3$ | 3-Cl$_3$—C$_6$H$_4$ | EP-A 463 488 |
| I.3D-3 | CH$_3$ | 4-CF$_3$—C$_6$H$_4$ | EP-A 585 751 |
| I.3D-4 | CH$_3$ | 3-CF$_3$—C$_6$H$_4$ | EP-A 585 751 |
| I.3D-5 | CH$_3$ | 4-CH$_3$—C$_6$H$_4$ | EP-A 463 488 |
| I.3D-6 | CH$_3$ | 3,5-Cl$_2$—C$_6$H$_3$ | EP-A 463 488 |
| I.3D-7 | CH$_3$ | 2-OCH$_2$CH$_3$-pyrimidin-2-yl | WO-A 92/13,830 |

TABLE I.3E

Compounds of the formula IA, where Q is phenyl, R' is —C(CONHCH$_3$)=NOCH$_3$, n has the value 0, R" is CH$_2$ON=CR$^\gamma$CR$^\delta$=NOR$^\epsilon$, R$_\gamma$, R$^\delta$ and R$^\epsilon$ having the meanings given below

| No. | R$^\gamma$ | R$^\delta$ | R$^\epsilon$ | Reference |
|---|---|---|---|---|
| I.3E-1 | CH$_3$ | CH$_3$ | CH$_3$ | WO-A 95/21154 |
| I.3E-2 | CH$_3$ | CH$_3$ | CH$_2$CH$_3$ | WO-A 95/21154 |
| I.3E-3 | CH$_3$ | C$_6$H$_5$ | CH$_3$ | WO-A 95/21154 |
| I.3E-4 | CH$_3$ | C$_6$H$_5$ | CH$_2$CH$_3$ | WO-A 95/21154 |
| I.3E-5 | CH$_3$ | 4-Cl—C$_6$H$_4$ | CH$_3$ | WO-A 95/21154 |
| I.3E-6 | CH$_3$ | 4-Cl—C$_6$H$_4$ | CH$_2$CH$_3$ | WO-A 95/21154 |
| I.3E-7 | CH$_3$ | 4-F—C$_6$H$_4$ | CH$_3$ | WO-A 95/21154 |

TABLE I.4A

Compounds of the formula IA, where Q is phenyl, R' is —C(CO$_2$CH$_3$)=CHCH$_3$, n has the value 0, R" is unsubstituted or substituted (het)aryloxymethylene, the unsubstituted or substituted (het)aryl group having the meanings given below

| No. | Unsubst. or subst. (het)aryl | Reference |
|---|---|---|
| I.4A-1 | 2-CH$_3$—C$_6$H$_4$ | EP-A 280 185 |
| I.4A-2 | 2,5-(CH$_3$)$_2$—C$_6$H$_3$ | EP-A 513 580 |
| I.4A-3 | 2,4-(CH$_3$)$_2$—C$_6$H$_3$ | EP-A 513 580 |
| I.4A-4 | 2,3,5-(CH$_3$)$_3$—C$_6$H$_2$ | EP-A 513 580 |
| I.4A-5 | 2-Cl,5-CH$_3$—C$_6$H$_3$ | EP-A 513 580 |
| I.4A-6 | 2-CH$_3$,4-C[CH$_3$]=NOCH$_3$—C$_6$H$_3$ | EP-A 513 580 |
| I.4A-7 | 1-[4-Cl—C$_6$H$_4$]-pyrazol-3-yl | DE-A 44 15 483.6 |

TABLE I.4B

Compounds of the formula IA, where Q is phenyl, R' is —C(CO$_2$CH$_3$)=CHCH$_3$, n has the value 0, R" is unsubstituted or substituted (het)aryloxy, the unsubstituted or substituted (het)aryl group having the meanings given below

| No. | Unsubst. or subst. (het)aryl | Reference |
|---|---|---|
| I.4B-1 | C$_6$H$_5$ | EP-A 513 580 |

TABLE I.4C

Compounds of the formula IA, where Q is phenyl, R' is —C(CO$_2$CH$_3$)=CHCH$_3$, n has the value 0, R" is CH$_2$ON=CR$^\gamma$CR$^\delta$=NOR$^\epsilon$, R$^\gamma$, R$^\delta$ and R$^\epsilon$ having the meanings given below

| No. | R$^\gamma$ | R$^\delta$ | R$^\epsilon$ | Reference |
|---|---|---|---|---|
| I.4C-1 | CH$_3$ | CH$_3$ | CH$_3$ | WO-A 95/21153 |
| I.4C-2 | CH$_3$ | CH$_3$ | CH$_2$CH$_3$ | WO-A 95/21153 |
| I.4C-3 | CH$_3$ | C$_6$H$_5$ | CH$_3$ | WO-A 95/21153 |
| I.4C-4 | CH$_3$ | C$_6$H$_5$ | CH$_2$CH$_3$ | WO-A 95/21153 |
| I.4C-5 | CH$_3$ | 4-Cl—C$_6$H$_4$ | CH$_3$ | WO-A 95/21153 |
| I.4C-6 | CH$_3$ | 4-Cl—C$_6$H$_4$ | CH$_2$CH$_3$ | WO-A 95/21153 |

TABLE I.5A

Compounds of the formula IA, where Q is phenyl, R' is —C(CO$_2$CH$_3$)=CHCH$_2$CH$_3$, n has the value 0, R" is unsubstituted or substituted (het)aryloxymethylene, the unsubstituted or substituted (het)aryl group having the meanings given below

| No. | Unsubst. or subst. (het)aryl | Reference |
|---|---|---|
| I.5A-1 | 2-CH$_3$—C$_6$H$_4$ | EP-A 513 580 |
| I.5A-2 | 2,5-(CH$_3$)$_2$—C$_6$H$_3$ | EP-A 513 580 |
| I.5A-3 | 2,4-(CH$_3$)$_2$—C$_6$H$_3$ | EP-A 513 580 |
| I.5A-4 | 2,3,5-(CH$_3$)$_3$—C$_6$H$_2$ | EP-A 513 580 |
| I.5A-5 | 2-Cl, 5-CH$_3$—C$_6$H$_3$ | EP-A 513 580 |
| I.5A-6 | 2-CH$_3$, 4-C[CH$_3$]=NOCH$_3$—C$_6$H$_3$ | EP-A 513 580 |

TABLE I.5B

Compounds of the formula IA, where Q is phenyl, R' is —C(CO$_2$CH$_3$)=CHCH$_2$CH$_3$, n has the value 0, R" is unsubstituted or substituted (het)aryloxy, the unsubstituted or substituted (het)aryl group having the meanings given below

| No. | Unsubst. or subst. (het)aryl | Reference |
|---|---|---|
| I.5B-1 | C$_6$H$_5$ | EP-A 513 580 |

TABLE I.5C

Compounds of the formula IA, where Q is phenyl, R' is —C(CO$_2$CH$_3$)=CHCH$_2$CH$_3$, n has the value 0, R" is CH$_2$ON=CR$^\gamma$CR$^\delta$=NOR$^\epsilon$, R$^\gamma$, R$^\delta$ and R$^\epsilon$ having the meanings given below

| No. | R$^\gamma$ | R$^\delta$ | R$^\epsilon$ | Reference |
|---|---|---|---|---|
| I.5C-1 | CH$_3$ | CH$_3$ | CH$_3$ | WO-A 957 21153 |
| I.5C-2 | CH$_3$ | CH$_3$ | CH$_2$CH$_3$ | WO-A 95/21153 |
| I.5C-3 | CH$_3$ | C$_6$H$_5$ | CH$_3$ | WO-A 95/21153 |
| I.5C-4 | CH$_3$ | C$_6$H$_5$ | CH$_2$CH$_3$ | WO-A 95/21153 |
| I.5C-5 | CH$_3$ | 4-Cl—C$_6$H$_4$ | CH$_3$ | WO-A 95/21153 |
| I.5C-6 | CH$_3$ | 4-Cl—C$_6$H$_4$ | CH$_2$CH$_3$ | WO-A 95/21153 |

TABLE I.6A

Compounds of the formula IA, where Q is phenyl, R' is —C(COCH$_3$)=NOCH$_3$, n has the value 0, R" is unsubstituted or substituted (het)aryloxymethylene, the unsubstituted or substituted (het)aryl group having the meanings given below

| No. | Unsubst. or subst. (het)aryl | Reference |
|---|---|---|
| I.6A-1 | 2-CH$_3$—C$_6$H$_4$ | EP-A 498 188 |
| I.6A-2 | 2,5-(CH$_3$)$_2$—C$_6$H$_3$ | EP-A 498 188 |
| I.6A-3 | 2,4-(CH$_3$)$_2$—C$_6$H$_3$ | EP-A 498 188 |
| I.6A-4 | 2,3,5-(CH$_3$)$_3$—C$_6$H$_2$ | EP-A 498 188 |
| I.6A-5 | 2-CH$_3$, 4-C[CH$_3$]=NOCH$_3$—C$_6$H$_3$ | EP-A 498 188 |

TABLE I.6B

Compounds of the formula IA, where Q is phenyl, R' is —C(COCH$_3$)=NOCH$_3$, n has the value 0, R" is unsubstituted or substituted (het)aryloxy, the unsubstituted or substituted (het)aryl group having the meanings given below

| No. | Unsubst. or subst. (het)aryl | Reference |
|---|---|---|
| I.6B-1 | C$_6$H$_5$ | EP-A 498 188 |
| I.6B-2 | 6-[2-CN—C$_6$H$_4$—O]-pyrimidin-4-yl | EP-A 498 188 |

TABLE I.7A

Compounds of the formula IA, where Q is phenyl, R' is
—C(COCH$_2$CH$_3$)=NOCH$_3$, n has the value 0, R" is unsubstituted or
substituted (het)aryloxymethylene, the unsubstituted or substituted
(het)aryl group having the meanings given below

| No. | Unsubst. or subst. (het)aryl | Reference |
| --- | --- | --- |
| I.7A-1 | 2-CH$_3$—C$_6$H$_4$ | EP-A 498 188 |
| I.7A-2 | 2,5-(CH$_3$)$_2$—C$_6$H$_3$ | EP-A 498 188 |
| I.7A-3 | 2,4-(CH$_3$)$_2$—C$_6$H$_3$ | EP-A 498 188 |
| I.7A-4 | 2,3,5-(CH$_3$)$_3$—C$_6$H$_2$ | EP-A 498 188 |
| I.7A-5 | 2-CH$_3$, 4-C[CH$_3$]=NOCH$_3$—C$_6$H$_3$ | EP-A 498 188 |

TABLE I.7B

Compounds of the formula IA, where Q is phenyl, R' is
—C(COCH$_2$CH$_3$)=NOCH$_3$, n has the value 0, R" is unsubstituted or
substituted (het)aryloxy, the unsubstituted or substituted (het)aryl
group having the meanings given below

| No. | Unsubst. or subst. (het)aryl | Reference |
| --- | --- | --- |
| I.7B-1 | C$_6$H$_5$ | EP-A 498 188 |
| I.7B-2 | 6-[2-CN—C$_6$H$_4$—O]-pyrimidin-4-yl | EP-A 498 188 |

TABLE I.8A

Compounds of the formula IA, where Q is phenyl,
R' is —N(OCH$_3$)=CO$_2$CH$_3$, n has the value 0, (I.8A)

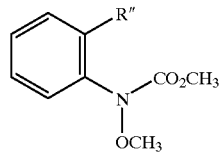

wherein R" is unsubstituted or substituted (het)aryloxymethylene,
the unsubstituted or substituted (het)aryl group having the
meanings given below

| No. | Unsubst. or subst. (het)aryl | Reference |
| --- | --- | --- |
| I.8A-1 | 2-CH$_3$—C$_6$H$_4$ | WO-A 93/15,046 |
| I.8A-2 | 2,5-(CH$_3$)$_2$—C$_6$H$_3$ | WO-A 93/15,046 |
| I.8A-3 | 2,4-(CH$_3$)$_2$—C$_6$H$_3$ | WO-A 93/15,046 |
| I.8A-4 | 2,3,5-(CH$_3$)$_3$—C$_6$H$_2$ | WO-A 93/15,046 |
| I.8A-5 | 2-Cl,5-CH$_3$—C$_6$H$_3$ | WO-A 93/15,046 |
| I.8A-6 | 2-CH$_3$, 4-C[CH$_3$]=NOCH$_3$—C$_6$H$_3$ | WO-A 93/15,046 |
| I.8A-7 | 2-CH$_3$, 4-C[CH$_3$]=NOCH$_2$CH$_3$—C$_6$H$_3$ | WO-A 93/15,046 |
| I.8A-8 | 2-CH$_3$, 4-C[CH$_2$CH$_3$]=NOCH$_3$—C$_6$H$_3$ | WO-A 93/15,046 |
| I.8A-9 | 2-CH$_3$, 4-C[CH$_2$CH$_3$]=NOCH$_2$CH$_3$—C$_6$H$_3$ | WO-A 93/15,046 |
| I.8A-10 | 1-[4-Cl—C$_6$H$_4$]-pyrazol-3-yl | DE-A 44 23 612.3 |

TABLE I.8B

Compounds of the formula IA, where Q is phenyl, R' is
—N(OCH$_3$)=CO$_2$CH$_3$, n has the value 0, R" is
CH$_2$ON=CR$^\alpha$R$^\beta$, R$^\alpha$ and R$^\beta$
have the meanings given below

| No. | R$^\alpha$ | R$^\beta$ | Reference |
| --- | --- | --- | --- |
| I.8B-1 | CH$_3$ | 3,5-Cl$_2$—C$_6$H$_3$ | WO-A 93/15,046 |

To produce a synergistic effect, fenazaquin and the active ingredient I are employed in a weight ratio in a range of from 20:1 to 1:20, in particular 10:1 to 1:10.

The invention also relates to a method of controlling harmful fungi, which comprises treating the fungi, their environment, or the materials, plants, seeds, soils, areas or spaces to be protected against fungal infection, with a composition as defined above, it being possible for the application of the active ingredients to be effected simultaneously, i.e. jointly or separately, or in succession.

The compositions according to the invention can be applied, for example, in the form of directly sprayable solutions, powders, suspensions, also highly concentrated aqueous, oily or other suspensions or dispersions, emulsions, oil dispersions, pastes, dusts, materials for spreading or granules by means of spraying, atomizing, dusting, spreading or pouring. The use forms depend on the intended purposes; in any case, they should guarantee the finest possible distribution of the active ingredients according to the invention.

Normally, the plants are sprayed or dusted with the active ingredients or the seeds of the plants are treated with the active ingredients.

The formulations are prepared in a known manner, e.g. by extending the active ingredient with solvents and/or carriers, if desired using emulsifiers and dispersants, it also being possible for other organic solvents to be used as auxiliary solvents if water is used as the diluent. Suitable auxiliaries are essentially: solvents, such as aromatics (e.g. xylene), chlorinated aromatics (e.g. chlorobenzenes) paraffins (e.g. mineral oil fractions), alcohols (e.g. methanol, butanol), ketones (e.g. cyclohexanone), amines (e.g. ethanolamine, dimethylformamide) and water; carriers, such as ground natural minerals (e.g. kaolins, clays, talc, chalk) and ground synthetic minerals (e.g. highly-disperse silica, silicates); emulsifiers, such as non-ionic and anionic emulsifiers (e.g. polyoxyethylene fatty alcohol ethers, alkylsulfonates and arylsulfonates) and dispersants, such as lignin-sulfite waste liquors and methylcellulose.

Suitable surfactants are the alkali metal, alkaline earth metal and ammonium salts of aromatic sulfonic acids, e.g. ligno-, phenol-, naphthalene- and dibutylnaphthalene-sulfonic acid, and of fatty acids, alkyl- and alkylarylsulfonates, alkyl sulfates, lauryl ether sulfates and fatty alcohol sulfates; and salts of sulfated hexa-, hepta- and octadecanoles, and also fatty alcohol glycol ethers, condensates of sulfonated naphthalene and its derivates with formaldehyde, condensates of naphthalene, or of the naphthalenesulfonic acids, with phenol and formaldehyde, polyoxyethylene octylphenyl ether, ethoxylated iso-octyl-, octyl- or nonylphenol, alkylphenyl polyglycol ethers and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding. the active substances with a solid carrier.

Granules, e.g. coated granules, impregnated granules and homogeneous granules, can be prepared by binding the active ingredients onto solid carriers. Solid carriers are mineral earths such as silica gel, silicas, silica gels, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phospate, ammonium nitrate, ureas, and products of vegetable origin, such as cereal meal, tree bark meal, wood meal and nutshell meal, cellulose powders, or other solid carriers. Examples of such preparations which comprise the active ingredients in a weight ratio of 1:1 are:

I. a solution of 90 parts by weight of the active ingredients and 10 parts by weight of N-methylpyrrolidone which is suitable for use in the formn of microdrops;
II. a mixture of 20 parts by weight of the active ingredients, 80 parts of xylene, 10 parts by weight of the adduct of 8 to 10 mol of ethylene oxide to 1 mol of oleic acid N-monoethanolamide, 5 parts by weight of calcium dodecylbenzenesulfonate, 5 parts by weight of the adduct of 40 mol of ethylene oxide to 1 mol of castor oil; a dispersion is obtained by finely dividing the solution in water;
III. an aqueous dispersion of 20 parts by weight of the active ingredients, 40 parts by weight of cyclohexanone, 30 parts by weight of isobutanol, 20 parts by weight of the adduct of 40 mol of ethylene oxide to 1 mol of castor oil;
IV. an aqueous dispersion of 20 parts by weight of the active ingredients, 25 parts by weight of cyclohexanol, 65 parts by weight of a mineral oil fraction of boiling point 210 to 280° C. and 10 parts by weight of the adduct of 40 mol of ethylene oxide to 1 mol of castor oil;
V. a mixture, ground in a hammer mill, of 80 parts by weight of the active ingredients, 3 parts by weight of sodium diisobutylnaphthalene-1-sulfonate, 10 parts by weight of the sodium salt of a lignosulfonic acid from a sulfide waste liquor and 7 parts by weight of pulverulent silica gel; a spray mixture is obtained by finely dividing the mixture in water;
VI. an intimate mixture of 3 parts by weight of the active ingredients and 97 parts by weight of finely divided kaolin; this dust comprises 3% by weight of active ingredient;
VII. an intimate mixture of 30 parts by weight of the active ingredients, 92 parts by weight of pulverulent silica gel and 8 parts by weight of paraffin oil which had been sprayed onto the surface of this silica gel; this formulation imparts good adhesion properties to the active ingredient;
VIII. a stable aqueous dispersion of 40 parts by weight of the active ingredients, 10 parts by weight of the sodium salt of a phenylsulfonic acid/urea/formaldehyde condensate, 2 parts by weight of silica gel and 48 parts by weight of water, it being possible for this dispersion to be diluted further;
IX. a stable or oily dispersion of 20 parts by weight of the active ingredients, 2 parts by weight of calcium dodecylbenzenesulfonate, 8 parts by weight of fatty alcohol polyglycol ether, 20 parts by weight of the sodium salt of a phenolsulfonic acid/urea/formaldehyde condensate and 88 parts by weight of a paraffinic mineral oil.

The compositions according to the invention are distinguished by an outstanding activity against a broad spectrum of phytopathogenic fungi, in particular against botrytis. Some of them act systemically (i.e. they can be taken up from the treated plant without any loss in activity and may be translocated within the plant) and can be employed as foliar- and soil-acting fungicides.

They are especially important for controlling a large number of fungi which infect a plurality of crop plants, such as wheat, rye, barley, oats, rice, maize, grass, cotton, soya, coffe, sugar cane, grapevine, fruit species, ornamentals and vegetable species such as cucumbers, beans and cucurbits, and the seeds of these plants.

The compositions are applied by treating the fungi, or the seeds, plants, materials or the soil to be protected against fungal infection, with a fungicidally active amount of the active ingredients.

Application is effected before or after infection of the materials, plants or seeds by the fungi.

Specifically, the compositions are suitable for controlling the following plant diseases:
*Erysiphe graminis* (powdery mildew) in cereals,
*Erysiphe cichoracearum* and *Sphaerotheca fuliginea* in cucurbits,
*Podosphaera leucotricha* in apples,
*Uncinula necator* in grapevines,
*Venturia inaequalis* (scab) in apples,
Helminthosporium species in cereals,
*Septoria nodorum* in wheat,
*Botrytis cinerea* (gray mold) in strawberries, grapevines,
*Cercospora arachidicola* in ground nuts,
*Pseudocercosporella herpotrichoides* in wheat, barley,
*Pyricularia oryzae* in rice,
Fusarium and Verticillium species in a variety of plants,
Alternaria species in vegetables and fruit,
Monilinia species in fruit, and
Sclerotinia species in oilseed rape and vegetables.

The use against botrytis is preferred.

The compositions can also be employed in the protection of materials (protection of wood), e.g. against Paecilomyces variotii.

In general, the fungicidal compositions comprise from 0.1 to 95, preferably from 0.5 to 90% by weight of active ingredient.

Depending on the nature of the desired effect, the rates of application are from 0.02 to 3 kg of active ingredient per ha.

In the treatment of seed, amounts of from 0.001 to 50 g, preferably 0.01 to 10 g, of active ingredient are generally required per kilogram of seed.

In the use form as fungicides, the compositions according to the invention can also comprise other active ingredients, e.g. herbicides, insecticides, growth regulators, fungicides, or else fertilizers.

A mixture with fungicides frequently results in a widening of the fungicidal spectrum of action.

The following list of fungicides together with which the compounds according to the invention can be used is intended to illustrate the possible combinations, but not to impose any limitations:
sulfur,
dithiocarbonate and their derivatives, such as
iron(III) dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfide,
ammonia complex of zinc (N,N-ethylenebisdithiocarbamate),
ammonia complex of zinc (N,N'-propylenebisdithiocarbamate),
zinc (N,N'-propylenebisdithiocarbamate),
N,N'-polypropylenebis(thiocarbamoyl)disulfide,
nitro derivates, such as
dinitro(1-methylheptyl)phenylcrotonate,
2-sec-butyl-4,6-dinitrophenyl-3,3-dimethylacrylate,
2-sec-butyl-4,6-dinitrophenylisopropyl carbonate,
di-isopropyl 5-nitroisophthalate;
heterocyclic substances, such as
2-heptadecyl-2-imidazoline acetate, 2,4-dichloro-6-(o-chloroanilino)-s-triazine,
O,O-diethyl phthalimidophosphonothioate,
5-amino-1-[bis (dimethylamino)phosphinyl]-3-phenyl-1,2,4-triazole,
2,3-dicyano-1,4-dithioanthraquinone,
2-thio-1,3-dithiolo[4,5-b]quinoxaline,
methyl 1-(butylcarbamoyl)2-benzimidazolecarbamate,
2-methoxycarbonylaminobenzimidazole,
2-(furyl-(2))benzimidazole,
2-(thiazolyl-(4))benzimidazole,
N-(1,1,2,2-tetrachloroethylthio)tetrahydrophthalimide,
N-trichloromethylthiotetrahydrophthalimide,
N-trichloromethylthiophthalimide,
N-dichlorofluoromethylthio-N',N'-dimethyl-N-phenylsulfuric diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
pyridine-2-thiol 1-oxide,
8-hydroxylquinoline or its copper salt,
2,3-dihydro-5-carboxanilido-6-methyl- 1,4-oxathiine,
2,3-dihydro-5-carboxanilido-6-methyl-1,4-oxathiine 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
N-cyclohexyl-2,5-dimethylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethyl acetate,
piperazine-1,4-diylbis(1-(2,2,2-trichloroethyl)formamide,
1-(3,4-dichloroanilino)-1-formylamino-2,2,2-trichloroethane,
2,6-dimethyl-N-tridecyl-morpholine or its salts,
2,6-dimethyl-N-cyclododecyl-morpholine or its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ethyl-1,3-dioxolan-2-yl-ethyl]-1H,1,2,4-triazole,
1-[2-(2,4-dichlorophenyl)-4-n-propyl-1,3-dioxolan-2-yl-ethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-2-butanone,
1-(4-chlorophenyl)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxyl-6-methylpyrimidine,
bis-(p-chlorophenyl)-3-pyridinemethanol,
1,2-bis-(3-ethoxycarbonyl-2-thioureido)benzene,
1,2-bis-(3-methoxycarbonyl-2-thioureido)benzene,
and a variety of fungicides, such as
dodecylguanidine acetate,
3-[3-(3,5-dimethyl)-2-oxycyclohexyl)-2-hydroxyethyl) glutarimide, hexachlorobenzene,
methyl N-(2,6-dimethylphenyl)-N-(2-furoyl)-DL-alaninate,
DL-N-(2,6-dimethylphenyl)-N-(2'-methoxyacetyl) alanine methyl ester,
N-(2,6-dimethylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine,
3-[3,5-dichlorophenyl-(5-methyl-5-methoxymethyl]-1,3-oxazolidine-2,4-dione,
3-(3,5-dichlorophenyl)-1-isopropylcarbamoylhydantoin,
N-(3,5-dichlorophenyl)-1,2-dirmethylcyclopropane-1,2-dicarboximide,
2-cyano-[N-(ethylaminocarbonyl)-2-methoximino] acetamide,
1-[2-(2,4-dichlorophenyl)pentyl]-1H-1,2,4-triazole,
2,4-difluoro-α-(1H-1,2,4-triazolyl-1-methyl)benzhydryl alcohol,
N-(3-chloro-2,6-dinitro-4-trifluoromethylphenyl)-5-trifluoromethyl-3-chloro-2-aminopyridine,
1-((bis(4-fluorophenyl)methylsilyl)methyl-1H-1,2,4-triazole.

The synergistic action of the compositions according to the invention is illustrated with the aid of the use examples which follow, where the compounds of the formula I.1 to I.7 were used active ingredients I:

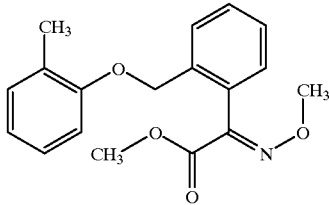

I.1

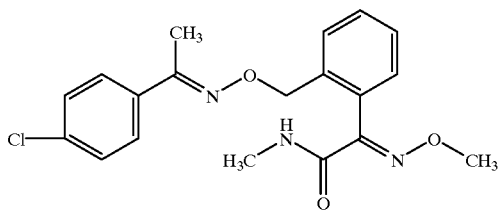

I.2

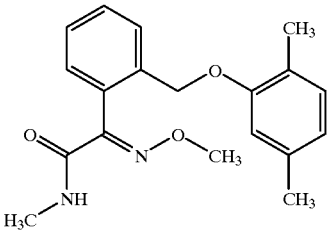

I.3

-continued

I.4
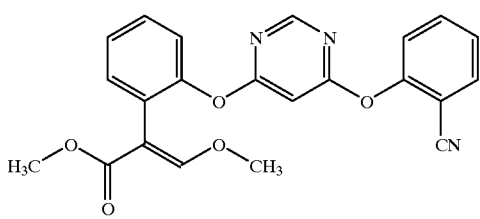

I.5
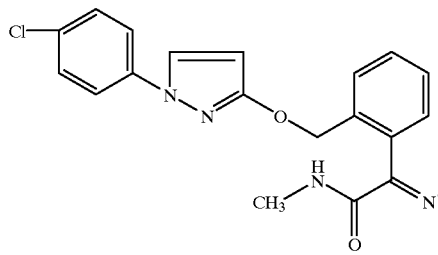

I.6
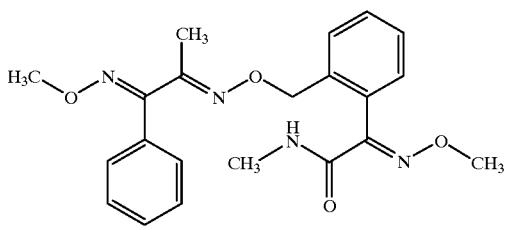

E,E isomer (comprises 5% of Z,E isomer)

I.7
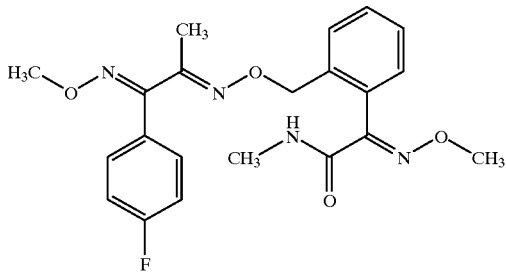

E,E side chain

USE EXAMPLE 1

Activity Against Botrytis Cinerea in Bell Peppers

Green bell pepper disks were sprayed to drip point with aqueous preparation of active ingredient, comprising 80% of active ingredient and 20% emulsifier in the dry matter. 2 hours after the spray coating had dried on, the fruit disks were inoculated with a spore suspension of Botrytis cinerea containing $1.7 \times 10^6$ spores per ml of a 2% strength Biomalz solution. The inoculated fruit disks were subsequently incubated for 4 days in humid chambers at 18° C. The Botrytis development on the diseased fruit disks was then evaluated visually (disease level 99%).

The visually determined data for the percentage of diseased fruit area were converted into efficacies as a percentage of the untreated control. An efficacy of 0 is the same disease level as the untreated control, an efficacy of 100 is a disease level of 0 percent. The efficacies to be expected for combinations of active ingredients were calculated using Colby's formula (Colby, S. R. (Calculating synergistic and antagonistic responses of herbicide Combinations", Weeds, 15, pp. 20–22, 1967) and compared with the observed efficacies. The results are shown in Table 1 below.

TABLE 1

| Active Compound | Concentration of active compound in ppm | | Degree of activity in % of control | |
|---|---|---|---|---|
| | Fenazaquin | I.1 | observed | calculated[*] |
| Control (untreated) | — | — | 0 | |
| Fenazaquin | 250 | — | 19 | |
| | 125 | — | 0 | |
| I.1 | — | 63 | 79 | |
| | — | 31 | 74 | |
| | — | 16 | 19 | |
| Fenazaquin + I.1 | 250 | 63 | 99 | 83 |
| | 250 | 31 | 85 | 79 |

[*]calculated according to the Colby formula

The test results show that the observed efficacy in all mixing ratios exceeds the additive efficacy calculated earlier using Colby's formula, i.e. a synergistic effect is present.

USE EXAMPLE 2

Activity Against Botrytis Cinerea

Pepper seedlings cv. "Neusiedler Ideal Elite" were grown until 4–5 leaves had developed properly and then sprayed to drip point with aqueous suspensions comprising 80% of active ingredient and 20% of emulsifier in the dry matter. After the spray coating had dried on, the plants were sprayed with a conidia suspension of the fungus Botrytis cinerea and placed into a chamber with high atmospheric humidity at 22–24° C. After 5 days, the disease on the untreated control plants had developed to such an extent that the leaf necroses formed covered a major portion of the leaves (disease level 83%).

The visually determined data for the percentage of diseased fruit area were converted into efficacies as a percentage of the untreated control. An efficacy of 0 is the same disease level as the untreated control, an efficacy of 100 is a disease level of 0 percent. The efficacies to be expected for combinations of active ingredients were calculated using Colby's formula (Colby, S. R. (Calculating synergistic and antagonistic responses of herbicide Combinations", Weeds, 15, pp. 20–22, 1967) and compared with the observed efficacies. The results are shown in Table 2 below.

TABLE 2

| Active Compound | Concentration of active compound in ppm | | Degree of activity in % of control | |
|---|---|---|---|---|
| | Fenazaquin | I.1 | observed | calculated[*] |
| Control (untreated) | — | — | 0 | |
| Fenazaquin | 500 | — | 4 | |
| | 250 | — | 4 | |
| I.1 | — | 63 | 28 | |
| | — | 31 | 16 | |

TABLE 2-continued

| Active Compound | Concentration of active compound in ppm | | Degree of activity in % of control | |
|---|---|---|---|---|
| | Fenazaquin | I.1 | observed | calculated[*)] |
| Fenazaquin + I.1 | 500 | 63 | 88 | 33 |
| | 250 | 31 | 70 | 19 |

[*)]calculated according to the Colby formula

The test results show that the observed efficacy in all mixing ratios exceeds the additive efficacy calculated earlier using Colby's formula, i.e. a synergistic effect is present.

USE EXAMPLE 3

Activity Against Botrytis Cinerea on Bell Peppers

Following the method described in Use Example 1, the following results were obtained using the compounds listed in Table 3 below:

TABLE 3

| Active Compound | Concentration of active compound in ppm | | Degree of activity in % of control | |
|---|---|---|---|---|
| | I.1–I.7 | Fenazaquin II | observed | calculated[*)] |
| control (untreated) | — | — | 0 | |
| Fenazaquin II | — | 500 | 0 | — |
| | | 250 | 0 | |
| | | 50 | 0 | |
| | | 25 | 0 | |
| I.2 | 50 | — | 95 | — |
| | 25 | | 89 | |
| I.3 | 50 | — | 79 | — |
| | 25 | | 28 | |
| I.4 | 50 | — | 15 | — |
| | 25 | | 34 | |
| I.5 | 50 | — | 60 | — |
| I.6 | 50 | — | 47 | — |
| | 25 | | 47 | |
| I.7 | 50 | — | 34 | — |
| | 25 | | 42 | |
| I.2 + II | 25 | 250 | 100 | 89 |
| | 25 | 25 | 95 | 89 |
| I.3 + II | 25 | 250 | 100 | 28 |
| | 25 | 25 | 79 | 28 |
| I.4 + II | 25 | 250 | 79 | 34 |
| | 25 | 25 | 66 | 34 |
| I.5 + II | 25 | 250 | 97 | 73 |
| | 50 | 50 | 79 | 60 |
| I.6 + II | 25 | 250 | 97 | 47 |
| | 25 | 25 | 76 | 47 |
| I.7 + II | 25 | 250 | 97 | 42 |
| | 25 | 25 | 84 | 42 |

[*)]calculated according to the Colby formula

The test results show that the observed efficacy in all mixing ratios exceeds the additive efficacy calculated earlier using Colby's formula, i.e. a synergistic effect is present.

USE EXAMPLE 4

Activity Against Botrytis Cinerea

Following the method described in Use Example 1, the following results were obtained using the compounds listed in Table 4 below:

TABLE 3

| Active Compound | Concentration of active compound in ppm | | Degree of activity in % of control | |
|---|---|---|---|---|
| | I.1–I.7 | Fenazaquin II | observed | calculated[*)] |
| Control (untreated) | | | 0 | |
| Fenazaquin II | | 500 | 48 | — |
| | | 250 | 27 | |
| | | 50 | 34 | |
| | | 25 | 17 | |
| I.2 | 25 | — | 0 | — |
| I.3 | 25 | — | 34 | — |
| I.4 | 50 | — | 0 | — |
| | 25 | | 0 | |
| I.5 | 50 | — | 0 | — |
| | 25 | | 0 | |
| I.6 | 50 | — | 52 | — |
| | 25 | | 72 | |
| I.7 | 25 | — | 62 | |
| I.2 + II | 25 | 25 | 59 | 17 |
| I.3 + II | 25 | 25 | 65 | 46 |
| I.4 + II | 50 | 500 | 90 | 48 |
| | 25 | 250 | 79 | 27 |
| | 50 | 50 | 52 | 34 |
| | 25 | 25 | 55 | 17 |
| I.5 + II | 50 | 50 | 52 | 34 |
| | 25 | 25 | 52 | 17 |
| I.6 + II | 50 | 500 | 97 | 75 |
| | 25 | 250 | 90 | 80 |
| | 50 | 50 | 86 | 68 |
| | 25 | 25 | 86 | 77 |
| I.7 + II | 25 | 25 | 90 | 68 |

[*)]calculated according to the Colby formula

The test results show that the observed efficacy in all mixing ratios exceeds the additive efficacy calculated earlier using Colby's formula, i.e. a synergistic effect is present.

Similar results are obtained when another individual compound from amongst those mentioned in Table I.1 to I.8 above are used in the above-described experiments.

We claim:

1. A synergistic composition for controlling harmful fungi comprising a solid or liquid carrier and synergistically effective amounts of fenazaquin, of the formula

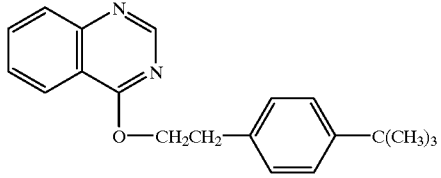

and at least one active ingredient I of the formula I.8A

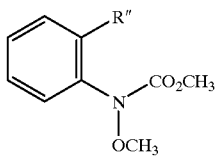

(1.8A)

wherein

R″ is phenoxymethylene or pyrazolyloxymethylene, wherein the phenyl and the pyrazolyl ring are unsubstituted or substituted by 1, 2 or 3 substituents selected from the group consisting of alkyl, halogen, $CF_3$, CHF$_2$, —C(CH$_3$)=NOCH$_3$ and phenyl which, in turn, is unsubstituted or substituted by 1, 2 or 3 halogen atoms and/or alkyl groups.

2. The composition defined in claim 1, wherein R" is pyrazolyloxymethylene, wherein the pyrazolyl ring is unsubstituted or substituted by 1, 2 or 3 substituents selected from the group consisting of alkyl, halogen, CF$_3$, CHF$_2$, —C(CH$_3$)=NOCH$_3$ and phenyl which, in turn, is unsubstituted or substituted by 1, 2 or 3 halogen atoms and/or alkyl groups.

3. The composition defined in claim 1, wherein R" is selected from the group consisting of 2-methylphenoxymethylene, 2,5-dimethylphenoxymethylene, 2,4-dimethylphenoxymethylene, 2,3,5-trimethylphenoxymethylene, 2-chloro-5-methylphenoxymethylene, 2-methyl-4-(1-methoxyiminoethyl)-phenoxymethylene, 2-methyl-4-(1-ethoxyiminoethyl)-phenoxymethylene, 2-methyl-4-(1-methoxyiminopropyl)-phenoxymethylene, 2-methyl-4-(1-ethoxyiminopropyl)-phenoxymethylene and 1-(4-chlorophenyl)pyrazol-3-yloxymethylene.

4. The composition defined in claim 1, wherein R" is 1-(4-chlorophenyl)pyrazol-3-yloxymethylene.

5. The composition defined in claim 1, wherein fenazaquin and the ingredient I are present in a weight ratio of from 20:1 to 1:20.

6. The composition defined in claim 2, wherein fenazaquin and the ingredient I are present in a weight ratio of from 20:1 to 1:20.

7. The composition defined in claim 3, wherein fenazaquin and the ingredient I are present in a weight ratio of from 20:1 to 1:20.

8. The composition defined in claim 4, wherein fenazaquin and the ingredient I are present in a weight ratio of from 20:1 to 1:20.

9. The composition defined in claim 1 which is conditioned in two parts, one part comprising the active ingredient I in a solid or liquid carrier, while the other part comprises fenazaquin in a solid or liquid carrier.

10. The composition defined in claim 2 which is conditioned in two parts, one part comprising the active ingredient I in a solid or liquid carrier, while the other part comprises fenazaquin in a solid or liquid carrier.

11. A method of controlling harmful fungi, which comprises treating the fungi, their environment, or materials, plants, seeds, soils, areas or spaces to be protected against fungal infection, with an effective amount of the composition in claim 1.

12. The method of claim 11, wherein R" is pyrazolyloxymethylene, wherein the pyrazolyl ring is unsubstituted or substituted by 1, 2 or 3 substituents selected from the group consisting of alkyl, halogen, CF$_3$, CHF$_2$, —C(CH$_3$)=NOCH$_3$ and phenyl which, in turn, is unsubstituted or substituted by 1, 2 or 3 halogen atoms and/or alkyl groups.

13. The method of claim 11, wherein R" is selected from the group consisting of 2-methylphenoxymethylene, 2,5-dimethylphenoxymethylene, 2,4-dimethylphenoxymethylene, 2,3,5-trimethylphenoxymethylene, 2-chloro-5-methylphenoxymethylene, 2-methyl-4-(1-methoxyiminoethyl)-phenoxymethylene, 2-methyl-4-(1-ethoxyiminoethyl)-phenoxymethylene, 2-methyl-4-(1-methoxyiminopropyl)-phenoxymethylene, 2-methyl-4-(1-ethoxyiminopropyl)-phenoxymethylene and 1-(4-chlorophenyl)pyrazol-3-yloxymethylene.

14. The method of claim 11, wherein R" is 1-(4-chlorophenyl)pyrazol-3-yloxymethylene.

15. The method of claim 11, wherein fenazaquin and the ingredient I are present in a weight ratio of from 20:1 to 1:20.

16. The method of claim 12, wherein fenazaquin and the ingredient I are present in a weight ratio of from 20:1 to 1:20.

17. The method of claim 13, wherein fenazaquin and the ingredient I are present in a weight ratio of from 20:1 to 1:20.

18. The method of claim 14, wherein fenazaquin and the ingredient I are present in a weight ratio of from 20:1 to 1:20.

19. A method of controlling harmful fungi, which comprises treating the fungi, their environment, or the materials, plants, seeds, soils, areas or spaces to be protected against fungal infection, with an effective amount of the synergistic composition defined in claim 9, the two separately conditioned parts being applied simultaneously or in succession.

20. A method of controlling harmful fungi, which comprises treating the fungi, their environment, or the materials, plants, seeds, soils, areas or spaces to be protected against fungal infection, with an effective amount of the synergistic composition defined in claim 10, the two separately conditioned parts being applied simultaneously or in succession.

* * * * *